United States Patent [19]

Alpegiani et al.

[11] Patent Number: 4,952,577
[45] Date of Patent: Aug. 28, 1990

[54] METHOXYMETHYL PENEM COMPOUNDS

[75] Inventors: Marco Alpegiani; Giovanni Franceschi; Ettore Perrone; Franco Zarini; Constantino Della Bruna, all of Milan, Italy

[73] Assignee: Farmitalia Carlo Erba S.r.l., Milan, Italy

[21] Appl. No.: 202,542

[22] Filed: Jun. 6, 1988

[30] Foreign Application Priority Data

Jun. 10, 1987 [GB] United Kingdom ............... 8713515

[51] Int. Cl.⁵ .................. C07D 499/00; A61K 31/425
[52] U.S. Cl. .................................. 514/192; 514/195; 540/310
[58] Field of Search ................. 540/310, 192, 193

[56] References Cited

U.S. PATENT DOCUMENTS 4,260,618 4/1981 Christensen et al. .
4,272,437 6/1981 Menard et al. .
4,482,565 11/1984 Foglio et al. .
4,558,042 12/1985 Foglio et al. .
4,631,150 12/1986 Battistini et al. .
4,692,442 9/1987 Gosteli et al. .

FOREIGN PATENT DOCUMENTS 0199446 10/1986 European Pat. Off. .
207387 9/1989 Japan .
2042515 9/1980 United Kingdom .

Primary Examiner—Nicholas S. Rizzo
Attorney, Agent, or Firm—Wegner & Bretschneider

[57] ABSTRACT

A substantially (≧95%) optically pure (5R,6S,1'R) penem of formula

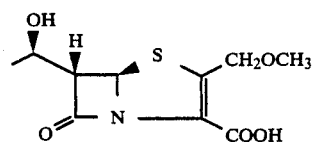

and the pharmaceutically acceptable salts and the ester prodrugs thereof, are endowed with antibacterial activity.

11 Claims, No Drawings

METHOXYMETHYL PENEM COMPOUNDS

The present invention provides optically pure, (5R,6S,1'R)-configured 6-(1-hydroxyethyl)-2-methoxymethyl-penem-3-carboxylic acid represented by the formula:

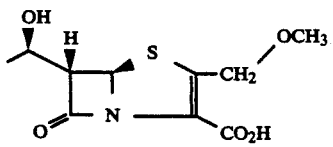

(I)

and pharmaceutically acceptable salts thereof and ester prodrugs thereof. These compounds may be presented as a pharmaceutical composition, also comprising a pharmaceutically acceptable carrier or diluent and are useful as antibacterial agents in the treatment of infections in humans and mammalian species.

Within the scope of the present invention, the term "optically pure" means that the (5R,6S,1'R)-configured product constitutes at least 95% of any mixture of possible stereoisomers thereof. The term "pharmaceutically acceptable salts" refers to non-toxic salts formed by salification of the carboxy group of the compound of formula (I) with an organic or inorganic base. The term encompasses alkali metal and alkaline earth metal salts, for example sodium, potassium, magnesium or calcium salts, and ammonium salts with ammonia or suitable organic amines, such as lower alkylamines, for example triethylamine, hydroxy-lower alkylamines and especially hydroxy ($C_{1-4}$-alkyl)amines, for example 2-hydroxyethylamine, bis-(2-hydroxyethyl) amine or tris-(2-hydroxyethyl) amine. Also encompassed are basic aliphatic esters such as di-(lower)alkylamino-$C_{2-6}$alkyl esters of lower amino alkylcarboxylic acids or of aminobenzoic acids exemplified by 4-aminobenzoic acid 2-diethylaminoethyl ester, lower alkylene-amines and especially ($C_{1-4}$-alkylene)amines, 1-ethylpiperidine, lower cycloalkylamines or dicycloalkylamines, for example dicyclohexylamine, benzylamines, for example N,N'-dibenzylethylenediamine, dibenzylamine or N-benzyl-β-phenethylamine, or basic aminoacids, for example arginine. The word "lower" as used herein in conjunction with alkyl or alkoxy moieties designates a preferred size of less than 7 carbon atoms.

Particularly preferred pharmaceutically acceptable salts of the compound of formula (I) are the sodium, potassium and arginine salts.

The term "ester prodrugs" refers to esters of the penem carboxylic acid of formula (I) that can be cleaved under physiological conditions, releasing the parent compound in vivo. In particular, the term refers to esters which can be absorbed from the gastro-intestinal tract after oral administration, and then are hydrolyzed in the bloodstream by aspecific serum esterases. Preferred ester prodrugs are those encompassed by the formula:

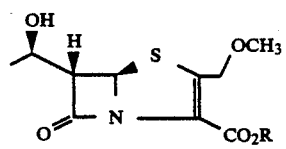

(II)

wherein R is (a) acyloxymethyl or 1-(acyloxy)ethyl;
(b) benzoyloxymethyl or 1-(benzoyloxy)ethyl, either unsubstituted or substituted on the ring by a free, methylated or acetylated hydroxy or amino group;
(c) lower alkoxycarbonyloxymethyl or 1- lower alkoxycarbonyloxy)ethyl;
(d) 3-phthalidyl;
(e) 2-oxo-1,3-dioxolan-4-yl, optionally substituted by a $C_1$-$C_4$ *alkyl group in the* 5 position;
(f) (2-oxo-1,3-dioxolen-4-yl)methyl, optionally substituted by a phenyl or $C_1$-$C_4$alkyl group at the 5 position;
(g) a group $CH_2CO_2R'$, wherein R' is $C_1$-$C_4$ *straight or branched alkyl, or benzyl*; or
(h) 2-oxotetrahydrofuran-5-yl, optionally substituted by a $C_1$-$C_4$alkyl group at the 4 position.

In the definition of R under (a) above the term "acyl" is intended to include straight or branched $C_2$-$C_{10}$alkanoyl or $C_4$-$C_8$cycloalkanoyl groups.

Particularly preferred ester prodrugs of the compound of formula (I) are those herein tabulated:

TABLE 1

| Compound | R |
|---|---|
| 1 | CH₂OCCH₃ <br> ‖ <br> O |
| 2 | CH₂OCC(CH₃)₃ <br> ‖ <br> O |
| 3 | CH₂OCCH₂CH₃ <br> ‖ <br> O |
| 4 | CH₂OCCH₂–⟨cyclohexyl⟩ <br> ‖ <br> O |
| 5 | CH₂OC–⟨cyclohexyl⟩ <br> ‖ <br> O |
| 6 | CH₂OC–⟨phenyl⟩ <br> ‖ <br> O |
| 7 | CH₂OC—CH(C₃H₇)₂ <br> ‖ <br> O |
| 8 | CHOCOCH₃ <br> \| <br> CH₃ |
| 9 | CHOCOCH₂–⟨cyclohexyl⟩ <br> \| <br> CH₃ |

TABLE 1-continued

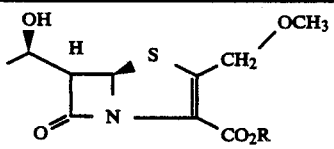

| Compound | R |
|---|---|
| 10 | CHOCO-C₆H₄(OCOCH₃) with CH₃ (structure shown) |
| 11 | CH₂OCOCH₃ |
| 12 | CH₂OCOCH₂CH₃ |
| 13 | CH₂OCOCH(CH₃)₂ |
| 14 | CH₂OCOCH₂-cyclohexyl |
| 15 | CH(CH₃)OCOCH₃ |
| 16 | CH(CH₃)OCOC₂H₅ |
| 17 | CHOCO-bornyl with CH₃ (structure shown) |
| 18 | phthalidyl (structure shown) |
| 19 | (5-methyl-2-oxo-1,3-dioxol-4-yl)methyl [shown with CH₃ on ring] |
| 20 | -CH₂-(5-methyl-2-oxo-1,3-dioxol-4-yl) |
| 21 | CH₂CO₂Et |
| 22 | CH₂CO₂C(CH₃)₃ |

TABLE 1-continued

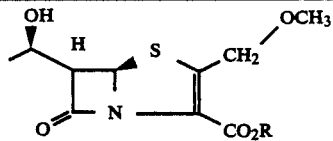

| Compound | R |
|---|---|
| 23 | -CH₂-(4-phenyl-2-oxo-1,3-dioxol-5-yl) -CH₂—C(Ph)=C—O—C(=O)—O |
| 24 | -CH₂-(2-oxo-1,3-dioxol-4-yl) |
| 25 | (5-methyl-2-oxo-tetrahydrofuran-yl) structure |

The compounds of the present invention can be manufactured by the following process
(a) by cyclization of a compound of formula (III)

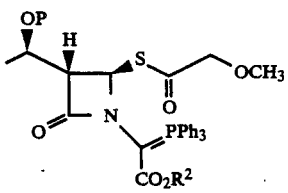

wherein P is either hydrogen or a hydroxy protecting group, and R² is either R, as defined in the formula (II) above, or is a carboxy protecting group;

(b) by cyclization of a compound of formula (IV)

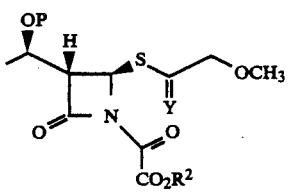

wherein P and R² are as defined above, and Y represents either oxygen or sulfur;

(c) by reaction of a compound of formula (I), or a salt thereof, prepared according to one of the routes (a) and (b) above, with a compound of formula (V)

R-X (V)

wherein R is as defined above and X is either chloro, bromo, iodo, mesyloxy, trifluoromethanesulfonyloxy, or tosyloxy, and, when P is different from hydrogen and R² is different from R, by removing the P and R² protecting groups, and if desired, by converting the resulting compound of formula (I) into a salt thereof, and/or by converting a resulting salt of the compound of formula (I) into the free compound, and/or by converting a salt of the compound of formula (I) into a different salt thereof. Preferred protecting groups P for the hydroxyl function are trimethylsilyl, tert-butyldimethyl silyl, tetrahydropyranyl, allyloxycarbonyl or p-nitrobenzyloxycarbonyl. When $R^2$, being different from R, is a carboxy protecting group, it is preferably allyl, p-nitrobenzyl or p-methoxybenzyl.

The conditions for the removal of said protecting groups are known per se. The cyclization of a compound of formula (III) is carried out by plain heating in an inert organic solvent, preferably benzene, toluene or dioxane, at reflux or near-to-reflux temperatures.

The cyclization of a compound of formula (IV) is carried out by treatment with trimethylphosphite or triethylphosphite in an inert or8anic solvent, such as chloroform, benzene, toluene, xylene or dioxane. The conditions for said cyclization, which depends on whether Y is oxygen or sulfur, are known-per-se and

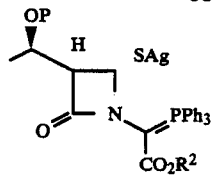

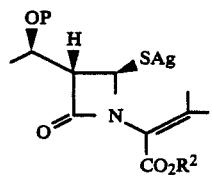

wherein P and $R^2$ are as defined above, and L is a leaving group, preferably acetoxy, benzyloxy, phenylsulfonyl or chloro, by known-per-se methodologies. They are summarized in the following scheme:

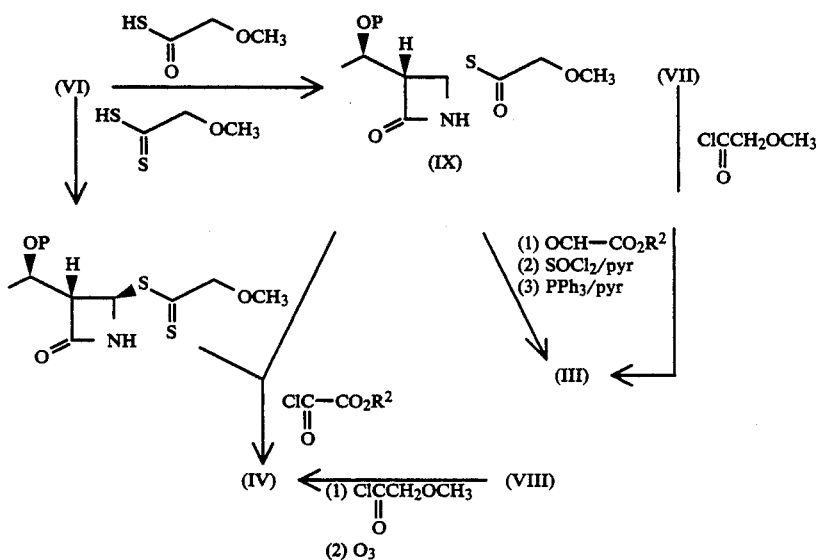

detailed in C. Battistini et al., Tetrahedron Lett. 25, 2595 (1984) and A. Yoshida et al., Chem. Pharm. Bull. 31, 768 (1983), and references therein. The reaction of a compound of formula (I), or a salt thereof, with a compound of formula (V) is carried out in an inert organic solvent, preferably dimethyl formamide, tetrahydrofuran, N-methylpyrrolidone, or dimethylsulfoxide, at temperatures ranging from −10° C. to +40°, preferably from 0° C. to +25° C., optionally in the presence of a base, such as sodium hydrogen carbonate, potassium carbonate, triethylamin or pyridine.

The intermediates of formulae (III), (IV) may be obtained by the following azetidinone precursors:

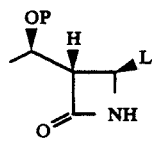

The compounds of formula (V), (VI), (VII), (VIII) are known or can be obtained from known compounds by known-per-se methodologies. The compound of formula (I) and its pharmaceutically acceptable salts offer the advantages of high antibacterial activity against gram-positive and gram-negative bacteria, combined with good pharmacokinetic properties when administered to humans or mammals. Owing to these properties and to their quite negligible toxicity, an excellent therapeutic index can be attained in this treatment of infections diseases caused by said micro-organisms. We have found that the optical purity of 6-(1'-hydroxyethyl)-2-methoxymethyl penem-3-carboxylic acid derivatives, in terms of the proportion of the (5R,6S, 1'R) -configured isomer present in an isomeric mixture, plays an essential role in the potency, width of spectrum, and chemoenzymatic stability of the product. Thus the sodium salt of the compound of formula (I), when compared with the complex mixture of racemic streoisomers disclosed in the U.S. Pat. No. 4,272,437, prepared as therein described (Example 36), showed an in vitro activity increased by a factor from 8 to 30, depending on the strain tested (Table 2). Moreover, compared with the prior-described mixture, the pure (5R,6S,1'R)-configured compound of formula (I), prepared as herein described, showed superior stability towards bacterial β-lactamases and renal dehydropeptidases, and a considerably improved chemical stability over the whole pH-range. These findings were confirmed by in vivo experiments (Table 3); indeed, while the sodium salt of the compound of formula (I) showed excellent efficacy in the control and treatment of experimental infections caused by gram-positive and gram-negative bacteria in the mouse, under the same experimental conditions the prior-art mixture showed no therapeutically useful levels of antimicrobial activity. When the two products were analyzed and compared, we found that the prior art mixture contained the (5R,6S,1'R)-configured epimer in such a minute amount to be hardly measurable by NMR integration. This finding is consistent with the results published for the epimeric mixture of a similar penem obtained by the same authors through the same route: Y. Ueda, A. Martel. J.-P. Daris, B. Belleau and M. Menard, Can. J. Chem. 60,904,1982. Thus, the major component of the prior art product was found to be the 5,6-cis-1-'R racemate, i.e. an equimolecular amount of the 5R,6R,1'R and 5S,6S,1'S enantiomers.

The compounds of formula (II), which are ester prodrugs of the compound of formula (I), offer the advantage of a very favourable bioavailability following oral administration. Their superior absorption from the gastro-intestinal tract, coupled with the good pharmacokinetic parameters proper of the compound of formula (I) that is released in vivo, results in higher and more prolonged plasma levels when compared with other penem ester prodrugs, for example with the most advanced compound of this type, FCE 22891 (G. Franceschi et al., J. Antibiotics 36, 938, 1983). This is apparent from Table 4, where the compounds n°1 and n°20 of the present invention are compared with the corresponding ester prodrugs of FCE 22101, namely FCE 22891 and FCE 23761.

The present invention includes pharmaceutical preparations for human or veterinary use containing the compound of formula (1), the pharmaceutically acceptable salts and prodrug esters thereof.

For oral administration, there are used tablets or gelatin capsules that contain a prodrug ester, preferably selected from those encompassed by the formula (II). still preferably selected from those listed in Table 1, together with diluents, for example lactose, dextrose, sucrose, mannitol, sorbitol. cellulose and/or glycine, and lubricants, for example silica, talc, stearic acid or salts thereof, such as magnesium or calcium stearate, and/or polyethylene glycol; tablets can also contain binders, for example magnesium aluminium silicate, starches, such as corn, wheat, rice or arrowroot starch, gelatin, tragacanth, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures or adsorbents, colourings, flavourings or sweeteners. For parenteral administration there are used infusion solutions, preferably isotonic aqueous solutions or suspension making it possible to prepare these before use, for example from lyophilised preparations. that contain the compound of formula (I),or a pharmaceutically acceptable salt thereof, preferably selected from the group consisting of the sodium, potassium or arginine salt, which may be present on its own or together with a carrier, for example mannitol. Such preparations may be sterilised and/or contain adjuncts, for example preservatives, stabilisers, wetting agents and/or emulsifiers, solubilisers, salts for regulating the osmotic pressure and/or buffers. The present pharmaceutical preparations, which, if desired, may contain other pharmacologically valuable substances, are manufactured in a manner known per se, for example by means of conventional mixing. dissolving or lyophilising processes, and contain from approximately 0.1% to 100%, especially from approximately 1% to approximately 50% or, in the case of lyphilisates, up to 100%, active ingredient.

Depending upon the type of infection and the condition of the infected organism, the daily dose used for the treatment of a warm-blooded animal (human or animal) weighing approximately 70 kg is from 125 mg to approximately 5 g.

TABLE 2

In vitro Antibacterial activity of the optically pure compound of formula (I), sodium salt and of the stereoisomeric mixture known and prepared according to U.S. Patent Specification 4,272,437, example 36.

| Microorganism | In vitro MIC (μg/ml) | |
| --- | --- | --- |
| | 5R,6S,1'R isomer | Stereoisomeric mixture |
| Staphylococcus aureus Smith | 0.09 | 0.78 |
| S. aureus 39/2 Pen+ | 0.09 | 6.25 |
| S. aureus 2 MR | 3.12 | >25 |
| S. aureus 2101 MR | 3.12 | >25 |
| S. aureus 5635 MR | 0.19 | 3.12 |
| S. epidermidis ATCC 12228 | 0.09 | 1.56 |
| Streptococcus pyogenes ATCC 12384 | 0.022 | 0.39 |
| S. salivarius ATCC 9758 | 0.022 | 0.19 |
| S. faecalis ATCC 6057 | 1.56 | >25 |
| S. faecalis 55 | 3.12 | >25 |
| S. faecium ATCC 8043 | 3.12 | >25 |
| Escherichia coli K 12 | 0.39 | 6.25 |
| E. coli R6K (TEM 1) | 0.39 | 12.5 |
| E. coli RP1 (TEM 2) | 0.78 | 25 |
| E. coli p453 (SHV-1) | 0.39 | 6.25 |
| E. coli R997 (HSM-1) | 0.39 | 6.25 |
| E. coli RGN238 (OXA-1) | 0.78 | 12.5 |
| E. coli R46 (OXA-2) | 0.39 | 12.5 |
| E. coli R57b (OXA-3) | 0.39 | 6.25 |
| E. coli B | 0.39 | 6.25 |
| E. coli B cef. R | 0.78 | >25 |
| Salmonella typhi ATCC 14028 | 0.39 | 6.25 |
| Shigella flexneri ATCC 11836 | 0.19 | 1.56 |
| Klebsiella aerogenes 1522E | 0.39 | 3.12 |
| K. Aerogenes 1082 E cef. R | 0.39 | 6.25 |
| Enterobacter cloacae 1321E | 0.39 | 3.12 |
| E. cloacae P99 cef. R. | 0.39 | 6.25 |
| E. aerogenes F46 | 0.78 | 12.5 |
| E. aerogenes 225 | 0.78 | 25 |
| Cirobacter freundii ATCC 8090 | 0.39 | 3.12 |
| C. freundii 4051 cef. R | 6.25 | >25 |
| Serratia marcescens ATCC 2902 | 6.25 | >25 |
| Acinetobacter calcoaceticus Bg 3 | 1.56 | >25 |
| A. calcolaceticus N 409 | 6.25 | >25 |
| Proteus mirabilis FI 7474 | 0.78 | 12.5 |
| P. rettgeri ATCC 925 | 1.56 | >25 |
| P. morganii ATCC 25830 | 1.56 | >25 |
| P. vulgaris 51 | 0.39 | 6.25 |
| Providencia stuartii Bs 60 | 3.12 | >25 |
| Pseudomonas aeruginosa 2598 | >25 | >25 |
| P. aeruginosa ATCC 19660 | >25 | >25 |

TABLE 3

Therapeutic efficacy against experimental infections in the mouse of the optically pure compound of formula (I), sodium salt, and of a representative prodrug ester thereof (Compound 20)

| Infections | Therapy after infection (hours) | $ED_{50}$ (mg/kg, cumulative dose) | |
|---|---|---|---|
| | | sodium salt[a] | ester (Comp.20)[b] |
| *Staphylococcus aureus* Smith | 2 | 0.21 | — |
| *Escherichia coli* G | 0.5-1.5-6 | 6.7 | 13.1 |

[a]subcutaneous administration
[b]oral administration

TABLE 4

Pharmacokinetic parameters of representative prodrug esters of the compound of formula (I) in comparison with the corresponding esters of FCE 22101

| Parameter | Compound[1] | | | |
|---|---|---|---|---|
| | Comp. 1 | Comparison (FCE 22891) | Comp. 20 | Comparison (FCE 23761) |
| AUC i.v. of parent drug[2] (μg. min/ml) | 920 | 307 | 920 | 307 |
| AUC os of prodrug | 763 | 151 | 745 | 85 |
| % Oral Bioavailability[3] | 83 | 49 | 81 | 27 |
| t½ os (min) { α | 7 | 6 | 7 | 9.5 |
| β | | | 13 | |

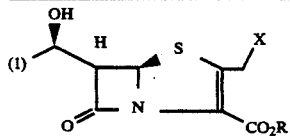

(1)

[2]At 20 mg/kg in the mouse (3) % Oral Bioavailability = $\frac{(AUC\ os)\ prodrug}{(AUC\ iv)\ drug} \times 100$ Compound 1: X = $OCH_3$, R = $CH_2OCOCH_3$ Compound 20: X = $OCH_3$, R = 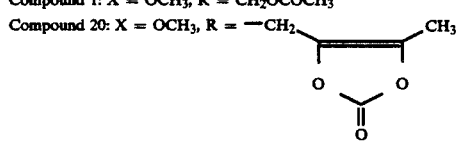

Comparison compounds have X = $OCONH_2$

EXAMPLE 1

Allyl (5R,6S)-6-[1(R) tert.Butyldimethylsilyloxy-ethyl]-2-Methoxymethyl Penem-3-Carboxylate (3S,4R)-1-[1-(Allyloxycarbonyl)-1-(Triphenylphosphoranyliden)methyl]-3-[1(R) tert.butyldimethylsilyloxyethyl]-4-(argentothio)-azetidin-2-one (727 m8) was dissolved in dry $CH_3CN$ (20 ml) and treated with methoxyacetyl chloride (110 ul). After stirring for 10 minutes at r.t, the reaction mixture was diluted with ethyl acetate, filtered through celite, washed with 5% aqueous sodium hydrogen carbonate then twice with brine. "r.t." means room temperature. After evaporating the solvent in vacuo, the residue was taken up in toluene (150 ml) and heated at reflux for 90 minutes. The solution was concentrated under reduced pressure then chromatographed (230-400 Mesh Silica Gel; cyclohexane-ethyl acetate 80/20 as eluant) affording the title product as a yellowish oil (360 mg; 87%)

IR $(CHCl_3) \nu$ 1785, 1700 $cm^{-1}$.

NMR (90 MHz, $CDCl_3$)δ: 0.09 (6H, s) 0.89 (9H, s) 1.26 (3H, d, J=6.5 Hz) 3.39 (3H, s) 3.67 (1H, dd, J=<2 and 7 Hz) 4.23 (1H, m) 4.5–4.8 (4H, m) 5.0–5.5 (2H, m) 5.56 (1H, d, J <2Hz) 5.55–6.05 (1H. m) ,

EXAMPLE 2

Allyl (5R,6S)-6-[1(R)Hydroxyethyl]-2-MethoxymethylPenem-3-Carboxylate

A solution of allyl (5R,6S)-6-[1(R) tert.butyldimethylsilyloxyethyl]-2-methoxymethylpenem-3-carboxylate (360 mg) in dry tetrahydrofuran (6 ml) was sequentially treated with acetic acid (0.6 ml) and tetrabutylammonium fluoride trihydrate (930 mg) under stirring.

The solution was let stand overnight at r.t., then concentrated to a small volume and chromatographed on silica gel (cyclohexane/ethyl acetate 1/1 as eluant) to give the title product as white powder (250 mg)

UV $(CHCl_3)$ λmax 326 nm.

EXAMPLE 3

Allyl (5R,6S)-6-[1(R)Hydroxyethyl]-2-Methoxymethyl-Penem-3-Carboxylate

A solution of (3S,4R)-1-[1-(allyloxycarbonyl)-1 -(triphenylphosphoranyliden) methyl]-3-[1(R)hydroxyethyl]-4-(argentothio)-azetidin-2-one (6.1 g) in dry acetonitrile (250 ml) at -10° C. was treated with methoxyacetyl chloride (1.2 ml), then stirring was continued 15 minutes at 0° C. Ethyl acetate was added and the resulting mixture was filtered over celite. The organic phase was washed with aqueous sodium hydrogen carbonate, dried over sodium sulphate and concentrated. Flash chromatography of the residue (Silica gel 230-400 Mesh; hexaneethyl acetate mixtures as eluants) gave (3S,4R)-1-[1-(allyloxycarbonyl)-1-(triphenylphosphoranyliden) methyl]-3-[1(R) hydroxyethyl]-4-(methoxyacetylthio)-azetidin- -2-one as yellowish foam (4.2 g).

The above prepared product was dissolved in toluene (250 ml) and refluxed 2 h. The residue, after cooling and removal of the solvent, was purified through silica gel chromatography (cyclohexane-ethyl acetate mixtures as eluants) affording the title product as white powder (2.5 g).

IR (KBr) ν 1775, 1705 cm⁻¹.
UV (EtOH) λmax 326 nm.

EXAMPLE 4

(5R,6S -6-[1(R)-Hydroxyethyl]-2-Methoxymethyl-Penem-3-Carboxylic Acid Sodium Salt Allyl (5R,6S)-6-[1(R) hydroxyethyl]-2-methoxymethylpenem-3-carboxylate (2.5 g), dissolved in dry tetrahydrofuran (60 ml), was sequentially treated with sodium ethyl hexanoate (1.05 g), triphenylphosphine (300 mg) and tetrakis (triphenylphosphine) palladium (0) (100 mg). Stirring was continued for 30', after which time TLC monitoring showed no more starting material was left. Diethyl ether (40 ml) was added and the precipitate was isolated by centrifugation. The crude material was dissolved in the minimum amount of water and purified by reverse-phase chromatography (LiChroprep ® RP C-18 Merck; water then water-acetone as eluants) the product containing fractions were collected and freeze-dried to afford the title product as white powder (1.8 g).

IR (KBr) ν 1755, 1600, 1575 cm⁻¹.
UV (H₂O) λmax 258 nm (ε=4044); λmax 306 nm (ε=6076).
NMR (200 MHz, D₂O) δ: 1.30 (3H,d, J=6.3Hz) 3.38 (3H,s) 3.91 (1H,dd, J=1.6 and 6.0 Hz) 4.25 (1H,m) 4.48 and 4.79 (2H, two d, J=14.0 Hz) 5.66 (1H,d, J=1.6 Hz).

EXAMPLE 5

Acetoxymethyl (5R,6S)-6-[1(R)-Hydroxyethyl]-2-Methoxymethyl-Penem-3-Carboxylate (5R,6S)-6-[1(R)hydroxyethyl]-2-methoxymethylpenem-3-carboxylic acid sodium salt (258 mg) in dry DMF (3 ml) was treated with acetoxymethylbromide (145 mg) at 0° C., then stirred 2 h at r.t. After partitioning between AcOEt and 2% aqueous NaHCO₃, the organic phase was washed twice with brine, then dried and concentrated in vacuo. Addition of diisopropyl ether to the crude product gave a white precipitate which was filtered and dried (220 mg).

IR (KBr)ν 3590, 1780, 1765, 1715, 1580 cm⁻¹.
UV (CHCl₃) λmax 327 nm.
NMR (CDCl₃,90 MHz) δ: 1.33 (3H,d, J=6.5 Hz) 2.12 (3H,s) 2.3 (1H, bs, exch D₂O) 3.39 (3H,s) 3.71 (1H,dd, J=<2 and 6.5 Hz) 4.17 (1H,m) 4.47 and 4.73 (2H, two d,J=16 Hz) 5.58 (1H,d J <2 Hz) 5.82 (2H, center of ABq).

EXAMPLE 6

(5-Methyl-2-Oxo-1,3-Dioxolen-4-yl)Methyl (5R,6S)-6-[1(R)-Hydroxyethyl]-2-Methoxymethyl-Penem-3-Carboxylate A solution of (5R,6S)-6-[1(R)-hydroxyethyl]-2-methoxymethylpenem-3-carboxylic acid sodium salt (258 mg) in dry DMF (3 ml) was treated with (5-methyl-2-oxo-1,3-dioxolen-4-yl)methylbromide (180 mg) and stirred at r.t. for 2 h. The reaction mixture was poured into ethyl acetate/water, the organic phase was washed twice with water, then dried and concentrated in vacuo. Treatment of the residue with diisopropyl ether gave white crystals (240 mg)

UV (CHCl₃) λmax 326 nm.
IR (IR) ν 3450, 1820, 1780, 1725, 1710 cm⁻¹.

NMR (CDCl₃,90 MHz) δ: 1.32 (3H,d, 6.5 Hz) 2.17 (3H,S) 2.37 (1H, bs, exch. D₂O) 3.38 (3H,S) 3.69 (1H,dd,<2 and 6.5 Hz) 4.20 (1H,m) 4.43 and 4.70 (2H, two d, J=16 Hz) 4.93 (2H,S) 5.60 (1H,d, J<2 Hz).

EXAMPLE 7

(5-Methyl-2-Oxo-1,3-Dioxolen-4-yl)Methyl (5R,6S)-6-[1(R)-Hydroxyethyl]-2-Methoxymethyl-Penem-3-Carboxylate Step A To a stirred solution of (3S,4R)-3-[1(R)trimethylsilyloxyethyl]-4-methoxyacetylthio azetidin-2-one (3.3 g) in dry toluene (35 ml) at 10° C., triethylamine (1.8 ml) was added, followed by dropwise addition of (5-methyl-2-oxo-1,3-dioxolen-4-yl) methyloxalyl chloride (2.7 g) in toluene (10 ml). The resulting solution was stirred 15' at r.t., then washed with water, 5% aqueous sodium hydrogen carbonate and water again. After drying over Na₂SO₄ the organic solution was concentrated to a volume of 20 ml. Triethylphosphite (4 ml) was added and the solution was refluxed for 5 h. The mixture was cooled to r.t., then washed three times with water then dried over sodium sulphate. Removal of the solvent and chromatography of the residue over silica gel (n.hexane-ethyl acetate as eluants) gave (5-methyl-2-oxo-1,3-dioxolen-4-yl) methyl (5R,6S)-6-[1(R)-trimethylsilyloxyethyl]-2-methoxymethyl-penem-3-carboxylate as a colourless oil (2.9 g).

Step B

The above said product was dissolved in 95% ethanol (160 ml) and acetic acid (2 ml) was added. After stirring 1 h at r.t. the mixture was concentrated under vacuum to dryness. Addition of diisopropyl ether (50 ml) gave white crystals, which were filtered off and dried (2.0 g).

UV (CHCl₃) λmax 326 nm,
IR (KBr) ν 3450, 1820, 1780, 1725, 1710, 1580 cm⁻¹.

What is claimed is:

1. A (5R, 6S, 1'R) penem of at least 95% optical purity of the formula:

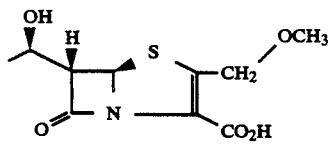
(I)

or a pharmaceutically acceptable salt thereof.

2. A compound according to claim 1, which is the sodium salt of the compound of formula (I).

3. A compound according to claim 1, which is the potassium salt of the compound of formula (I).

4. A compound according to claim 1, which is a salt of the compound of formula (I) with a (C₁-C₄alkylene)amine, a benzylamine, a hydroxy-(C₁-C₄alkyl)amine, a basic aliphatic ester of a carboxylic acid or a basic aminoacid.

5. A compound according to claim 1, which is the arginine salt of the compound of formula (I).

6. A compound which has the formula:

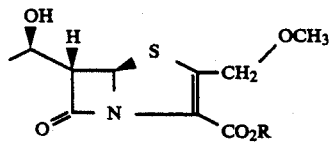
(II)

wherein R is
(a) acyloxymethyl or 1-(acyloxy)ethyl;
(b) benzoyloxymethyl or 1-(benzoyloxy)ethyl, either unsubstituted or ring-substituted by a free, methylated or acetylated hydroxy or amino group;
(c) alkoxycarbonyloxymethyl or 1-(alkoxycarbonyloxy)ethyl;
(d) 3-phthalidyl;
(e) 2-oxo-1,3-dioxolan-4-yl, optionally substituted by a $C_1$-$C_4$alkyl group in the 5 position;
(f) (2-oxo-1,3-dioxolen-4-yl)methyl, optionally substituted by a phenyl or $C_1$-$C_4$alkyl group at the 5 position;
(g) a group $CH_2CO_2R'$, wherein R' is $C_1$-$C_4$ straight or branched alkyl, or benzyl; or
(h) 2-oxotetrahydrofuran-5-yl, optionally substituted by a $C_1$-$C_4$alkyl group at the 4 position.

7. A compound according to claim 6 wherein R is pivaloyloxymethyl, propionyloxymethyl, cyclohexylacetoxymethyl, cyclohexanecarboxymethyl, dipropylacetoxymethyl, 1-(acetoxy)ethyl, 1-(cyclohexylacetoxy)ethyl, 1-(1-acetylsalicyloxy)ethyl, methoxycarbonyloxymethyl, ethoxycarbonyloxymethyl, isopropoxycarbonyloxymethyl, cyclohexylmethoxycarbonyloxymethyl, 1-(methoxycarbonyloxy)ethyl, 1-(ethoxycarbonyloxy)ethyl, 1-(bornyloxycarbonyloxy)ethyl, 3-phthalidyl, 2-oxo-1,3-dioxolan-4-yl, (5-methyl-2-oxo-1,3-dioxolen-4-yl) methyl, ethoxycarbonylmethyl, tert-butoxycarbonylmethyl, (5-phenyl-2-oxo-1,3-dioxolen-4-yl)methyl, (2-oxo-1,3-dioxolen-4-yl)methyl or 2-oxotetrahydrofuran-5-yl.

8. A compound according to claim 6, which is acetoxymethyl 6-(1-hydroxyethyl)-2-methoxyoxymethylpenem-3-carboxylate.

9. A compound according to claim 6, which is (2-oxo-1,3-dioxolen-4-yl)methyl 6-(1-hydroxyethyl)-2-methoxymethylpenem-3-carboxylate.

10. An antibacterial composition comprising an antibacterially effective amount of a compound of claim 1 or a pharmaceutically acceptable salt thereof and a pharmaceutically acceptable carrier or diluent.

11. An antibacterial composition comprising an antibacterially effective amount of a compound of claim 6 or a pharmaceutically acceptable salt thereof and a pharmaceutically acceptable carrier or diluent.

* * * * *